US008805505B1

(12) United States Patent
Roberts

(10) Patent No.: US 8,805,505 B1
(45) Date of Patent: Aug. 12, 2014

(54) USING TELEMETRY DOWNLINK FOR REAL TIME CLOCK CALIBRATION

(71) Applicant: Medtronic, Inc., Minneapolis, MN (US)

(72) Inventor: Melvin P. Roberts, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/749,852

(22) Filed: Jan. 25, 2013

(51) Int. Cl.
*A61N 1/00* (2006.01)

(52) U.S. Cl.
USPC .......................................................... 607/27

(58) Field of Classification Search
USPC .......................................................... 607/27
See application file for complete search history.

(56) References Cited

U.S. PATENT DOCUMENTS

| 5,153,824 | A | 10/1992 | Lalanne et al. |
| 5,740,129 | A | 4/1998 | Frampton |
| 6,453,196 | B1 * | 9/2002 | Von Arx et al. ............. 607/9 |
| 6,885,254 | B2 | 4/2005 | Kranz |
| 7,028,206 | B2 | 4/2006 | Waller |
| 7,200,507 | B2 | 4/2007 | Chen et al. |
| 7,348,822 | B2 | 3/2008 | Baer |
| 7,576,689 | B2 | 8/2009 | Weedon |
| 7,936,200 | B2 | 5/2011 | Abouda et al. |
| 8,085,099 | B2 | 12/2011 | Pancholi et al. |
| 2005/0114725 | A1 | 5/2005 | Patel et al. |
| 2005/0221870 | A1 | 10/2005 | Erdelyi et al. |
| 2006/0140320 | A1 | 6/2006 | Jensen et al. |
| 2010/0177588 | A1 | 7/2010 | Kaiwa et al. |
| 2012/0112804 | A1 | 5/2012 | Li et al. |
| 2012/0223757 | A1 | 9/2012 | Camp |
| 2013/0238048 | A1 * | 9/2013 | Almendinger et al. ......... 607/40 |

OTHER PUBLICATIONS

U.S. Appl. No. 13/749,947 "Using High Frequency Crystal From External Module to Trim Real Time Clock" to Mel Roberts, Jan. 25, 2013.

* cited by examiner

*Primary Examiner* — Robert N Wieland
(74) *Attorney, Agent, or Firm* — Evans M. Mburu

(57) ABSTRACT

An implantable medical device includes a local clock generator for generating a system clock signal. The local clock generator is periodically calibrated to maintain accuracy of the generated system clock signal. A clocking circuit is coupled to the local clock generator to provide the calibration factor for calibrating the local clock generator. The implantable medical device receives an accurate clock signal that is transmitted from an external device and the accurate clock signal is provided to the clocking circuit. The system clock signal is also provided to the clocking circuit and a computation is performed to derive the calibration factor.

16 Claims, 8 Drawing Sheets

USING TELEMETRY DOWNLINK FOR REAL TIME CLOCK CALIBRATION

FIELD

This disclosure relates to implantable medical devices. More specifically, the disclosure relates to methods and systems for improving and maintaining the accuracy of a clock generator of the implantable medical devices.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Some medical devices may be "leadless" and include one or more electrodes on an outer housing of the medical device to deliver therapeutic electrical signals to organs or tissues and/or sense intrinsic electrical signals or physiological parameters of a patient.

Implantable cardiac pacemakers or cardioverter-defibrillators, for example, provide therapeutic electrical signals to the heart, e.g., via electrodes carried by one or more medical leads or via electrodes on an outer housing of a leadless implantable medical device. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Numerous of the functions of the implantable medical device are controlled as a function of a local system clock that is included within the implantable medical device. The local clock may include an oscillator that generates an oscillator signal that causes the counter to increment its count. For example, an oscillator signal having a frequency of one megahertz may cause a counter to increment its count every microsecond, i.e. to count microseconds. Higher frequency oscillators may be used to provide higher time resolutions. A local time may be associated with a counter by incrementing the counter with a value other than one. For example an oscillator having a frequency of 250 kHz may be used to increment a counter by four every four microseconds in order to maintain a time count in microseconds. A value by which a counter is incremented depends on the rate of its oscillator compared to a time increment to be counted.

The implantable medical devices are also preferred to have a small housing form factor to enable an unobtrusive implantation within a patient. In the case of leadless implantable medical devices, the housing form factor must be extremely small to enable implantation within or adjacent to organs or tissue. For example, a leadless pacemaker may be implanted directly into a ventricle of the heart. The battery consumption is always a concern when designing implantable medical devices, but this concern is increased for small form factor devices that can only accommodate a small battery canister. A competing design requirement for implantable medical devices is high accuracy clocking signals. High clocking accuracy is needed to ensure accurate sensing and delivery of therapeutic electrical signals. However, generating the high accuracy clocking signals consume a substantial amount of current. On the other hand, the frequency of oscillators associated with low-power clocks changes over time due to poor long-term stability, temperature characteristics, and/or other environmental factors. Therefore, a need remains for clocks that consume little power yet having improved accuracy.

SUMMARY

In general, this disclosure describes techniques for periodically performing a calibration routine to calibrate a low-power local system clock within an implantable medical device based on an accurate clock signal having a frequency that is different from the signal of the low-power local system clock. The techniques include receiving the accurate clock signal and computing a calibration factor based on a difference between the accurate clock signal and a first clock signal generated by the local system clock. An operation of the local system clock is adjusted to compensate for a deviation from the accurate clock signal.

In an embodiment, the disclosure is directed to an implantable medical device that includes a processor, an input node for receiving a clock signal generated by the accurate clock, a local system clock that comprises a low power oscillator, and a clocking circuit that periodically performs a calibration routine to calibrate the local clock based on the accurate clock signal. The local clock may be continuously powered to generate first clock signals according to which the processor operates the implantable medical device.

In some embodiments, the accurate clock signal may have a first frequency and the first clock signal may have a second frequency that is different from the first frequency. A weighting factor may be provided for the computation of the calibration factor based on the relative difference between the first frequency and the second frequency.

In another embodiment, the disclosure is directed to a method that includes operating an implantable medical device in accordance with a local clock that comprises a low power oscillator clock included in the implantable medical device, and periodically performing a calibration routine to calibrate the local clock based on an accurate clock signal.

The foregoing summary information is intended to merely illustrate some of the aspects and features of the present disclosure and is not meant to limit the scope in any way. In fact, upon review of the foregoing and the following described and depicted embodiments, one of skill in the art will surely recognize insubstantial modifications or extensions of the disclosure each of which is expressly intended to be covered hereby. The disclosure is also not limited to the specific-described embodiments; rather, the constituent elements in each embodiment may be combined as appropriate and the combination thereof may effectively serve as an embodiment of the present disclosure. Such embodiments along with modifications are also within the scope of the present disclosure.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

Figure 1:
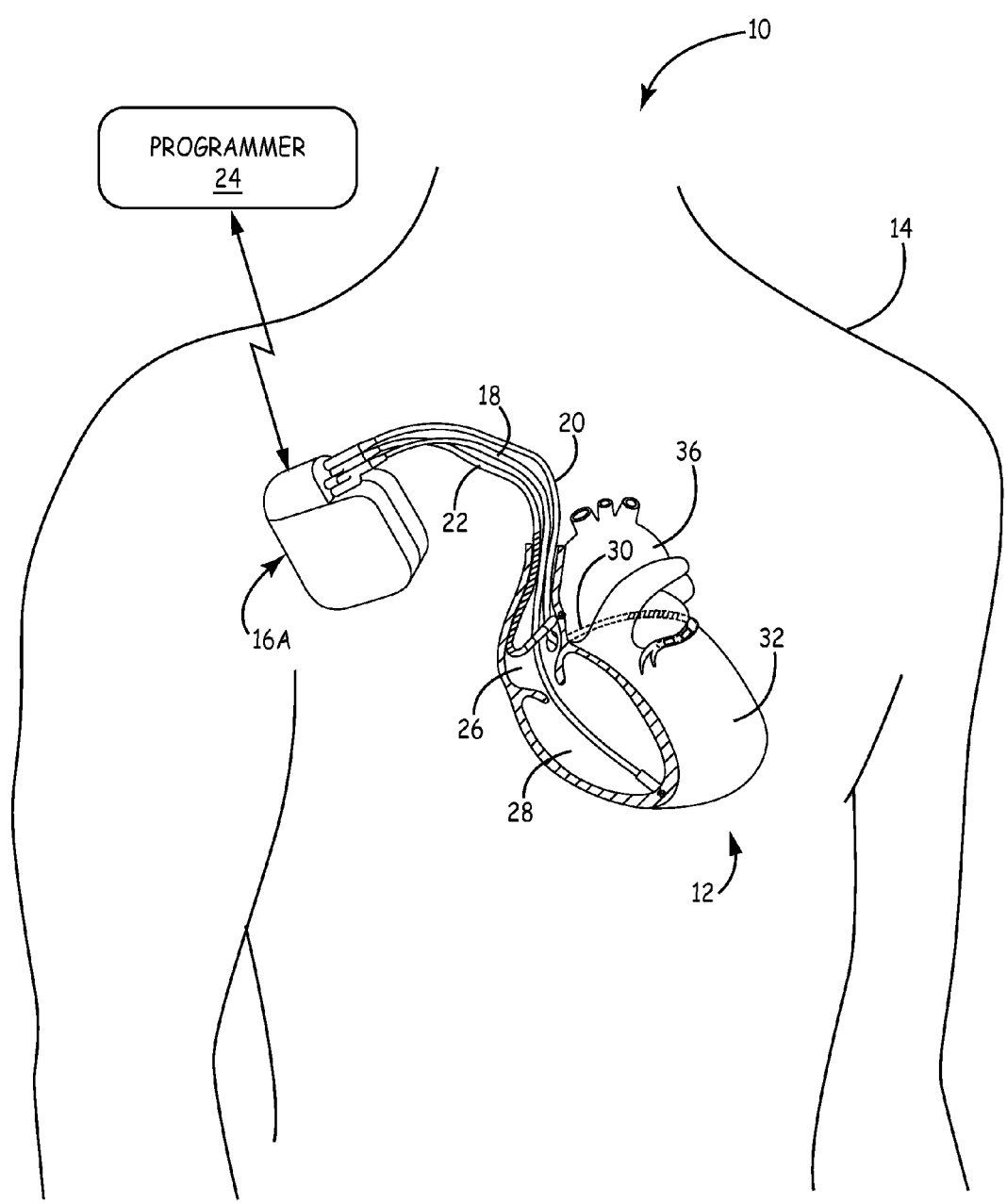
FIG. 1 depicts a conceptual diagram illustrating an embodiment of a therapy system that may be used to provide therapy to a heart of a patient.

The following detailed description is merely exemplary in nature and is not intended to limit the disclosure or the application and uses of the disclosure. Furthermore, there is no intention to be bound by any expressed or implied theory presented in the preceding technical field, background, brief summary or the following detailed description.

In general, this disclosure describes techniques for periodically performing a calibration routine to calibrate a low-power local clock within an implantable medical device (IMD). In an embodiment, the calibration may be based on an accurate clock signal provided by a clock residing within the IMD. As used in this disclosure, an accurate signal source refers to a signal generator that generates a signal having the desired properties, such as timing or frequency, which is utilized to set the baseline timing of the local clock. In another embodiment, the calibration may be based on a signal provided by an external device. As used in this disclosure, the external device is a device other than the IMD which will generally be external to the implant environment of the IMD. The external device may include another implantable medical device, although it is generally contemplated that the external device will not be implanted. In an embodiment, the signal may be a remote clock signal or a signal such as a data signal, or a control or command signal any of which may be telemetered to the implantable medical device by the external device. Such a remote signal may include the radio frequency (RF) synchronization data stream that may be included in the header of a telemetry communication message.

The techniques provide a low power oscillator for generating clock signals to control the IMD functionality. An example of a low-power local clock is a system clock that is powered continuously to control operation of the IMD. The low-power local clock may be calibrated periodically based on a signal generated by a high accuracy oscillator to correct the inaccuracies of the low-power local clock. The calibration allows accurate adjustment of the low-power local clock to compensate for errors due to trim resolution, circuit noise and temperature. The techniques disclosed herein may be employed within an IMD, such as an implantable pacemaker or an implantable leadless pacemaker, to reduce current drain by the clocking system of the IMD. In one example, the techniques may reduce total clocking system current drain in an IMD to less than 60 nanoamperes (nA).

Similar techniques described in this disclosure may be used to calibrate other local low-power local clocks included in an IMD, such as a telemetry polling clock and a telemetry linking clock used to operate a telemetry module of the IMD. For example, the techniques may include periodically performing a calibration routine to calibrate a telemetry polling clock, according to which the telemetry module monitors for a telemetry downlink. In some examples, the local clock and the additional clocks may be simultaneously calibrated.

FIG. 1 depicts a conceptual diagram illustrating an embodiment of a therapy system 10A that may be used to provide therapy to heart 12 of patient 14. Patient 14 ordinarily, but not necessarily, will be a human. Therapy system 10A includes IMD 16A, which is coupled to leads 18, 20, and 22, and programmer 24. IMD 16A may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver a therapy that may be in the form electrical stimulation to heart 12. In the example shown in FIG. 1, right ventricular lead 18 extends through one or more veins (not shown), the superior vena cava (not shown), and right atrium 26, and into right ventricle 28. Left ventricular coronary sinus lead 20 extends through one or more veins, the vena cava, right atrium 26, and into the coronary sinus 30 to a region adjacent to the free wall of left ventricle 32 of heart 12. In alternative embodiments, the LV lead 20 may also be introduced into the left ventricle through the septal wall. Right atrial lead 22 extends through one or more veins and the vena cava, and into the right atrium 26 of heart 12.

IMD 16A may sense electrical signals attendant to the depolarization and repolarization of heart 12 via electrodes (not shown in FIG. 1) coupled to at least one of the leads 18, 20, 22. In some examples, IMD 16A provides pacing pulses to heart 12 based on the electrical signals sensed within heart 12. The configurations of electrodes used by IMD 16A for sensing and pacing may be unipolar or bipolar. IMD 16A may also provide defibrillation therapy and/or cardioversion therapy via electrodes located on at least one of the leads 18, 20, 22. IMD 16A may detect arrhythmia of heart 12, such as fibrillation of ventricles 28 and 32, and deliver defibrillation therapy to heart 12 in the form of electrical pulses. In some examples, IMD 16A may be programmed to deliver a progression of therapies, e.g., pulses with increasing energy levels, until a fibrillation of heart 12 is stopped. IMD 16A detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT)

display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD.

For example, the user may use programmer 24 to retrieve information from IMD 16A regarding the rhythm of heart 12, trends therein over time, or tachyarrhythmia episodes. As another example, the user may use programmer 24 to retrieve information from IMD 16A regarding other sensed physiological parameters of patient 14, such as intracardiac or intravascular pressure, activity, posture, respiration, or thoracic impedance. As another example, the user may use programmer 24 to retrieve information from IMD 16A regarding the performance or integrity of IMD 16A or other components of system 10A, such as leads 18, 20, and 22, or a power source of IMD 16A.

The user may use programmer 24 to program a therapy progression, select electrodes used to deliver defibrillation shocks, select waveforms for the defibrillation shock, or select or configure a fibrillation detection algorithm for IMD 16A. The user may also use programmer 24 to program aspects of other therapies provided by IMD 16A, such as cardioversion or pacing therapies. In some examples, the user may activate certain features of IMD 16A by entering a single command via programmer 24, such as depression of a single key or combination of keys of a keypad or a single point-and-select action with a pointing device.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

Figure 2:
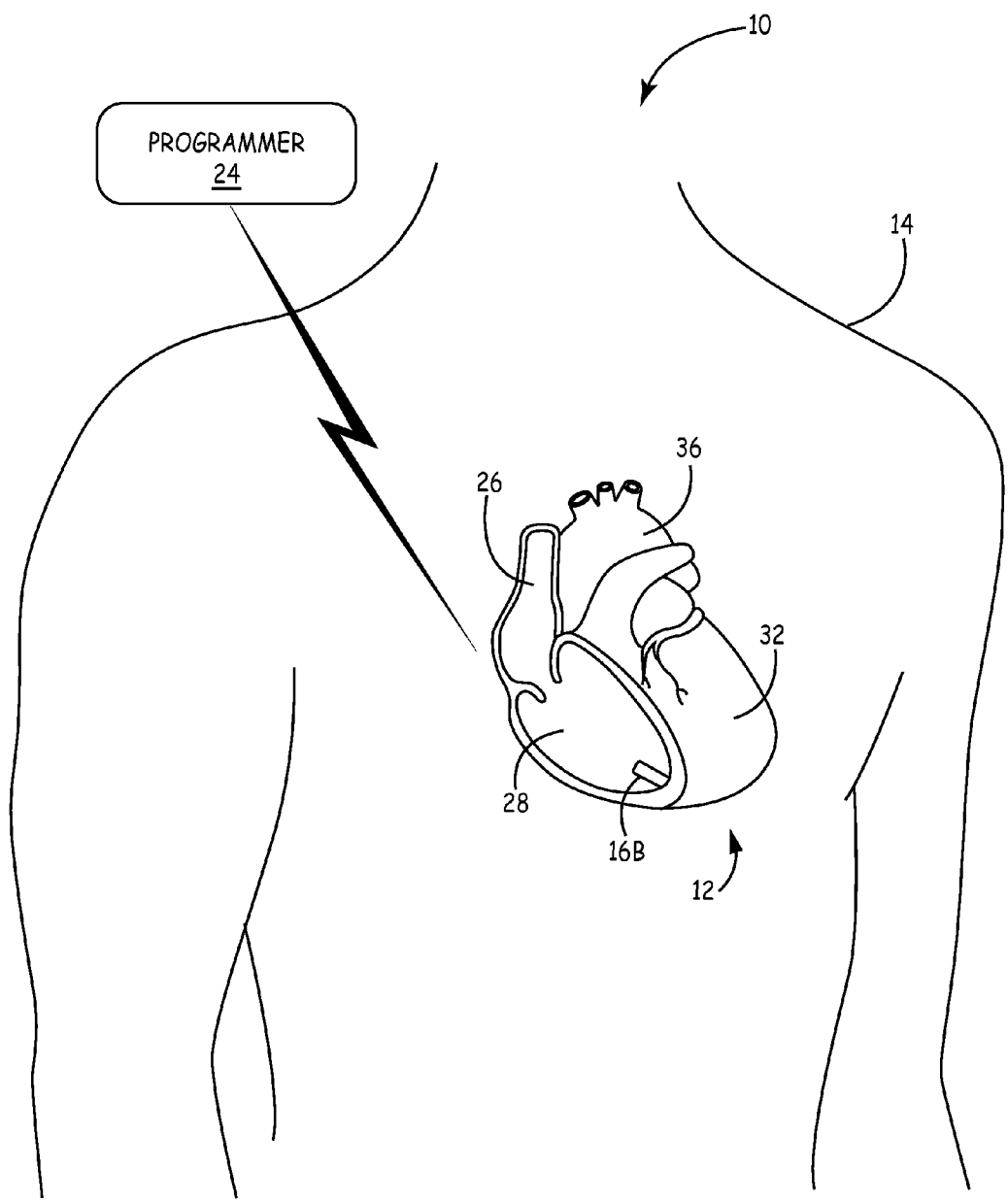
FIG. 2 illustrates another embodiment of a conceptual diagram of a therapy system that may be used to monitor one or more physiological parameters of patient and/or to provide therapy to a heart of a patient.

FIG. 2 illustrates another embodiment of a conceptual diagram of a therapy system 10B that may be used to monitor one or more physiological parameters of patient 14 and/or to provide therapy to heart 12 of patient 14. Therapy system 10B includes an implantable medical device (IMD) 16B, which is coupled to programmer 24. IMD 16B may be an implantable leadless pacemaker that provides electrical signals to heart 12 via one or more electrodes (not shown in FIG. 2) on its outer housing. Additionally or alternatively, IMD 16B may sense electrical signals attendant to the depolarization and repolarization of heart 12 via electrodes on its outer housing. In some examples, IMD 16B provides pacing pulses to heart 12 based on the electrical signals sensed within heart 12.

In the example of FIG. 2, IMD 16B is positioned wholly within heart 12 with one end proximate to the apex of right ventricle 28 to provide right ventricular (RV) pacing. Although IMD 16B is shown within heart 12 and proximate to the apex of right ventricle 28 in the example of FIG. 2, IMD 16B may be positioned at any other location outside or within heart 12. For example, IMD 16B may be positioned outside or within right atrium 26, left atrium 36, and/or left ventricle 32, e.g., to provide right atrial, left atrial, and left ventricular pacing, respectively. Depending in the location of implant, IMD 16B may include other stimulation functionalities. For example, IMD 16B may provide atrioventricular nodal stimulation, fat pad stimulation, vagal stimulation, or other types of neurostimulation. In other examples, IMD 16B may be a monitor that senses one or more parameters of heart 12 and may not provide any stimulation functionality. In some examples, system 10B may include a plurality of leadless IMDs 16B, e.g., to provide stimulation and/or sensing at a variety of locations.

FIG. 2 further depicts programmer 24 in communication with IMD 16B. As described above with respect to IMD 16A of FIG. 1, programmer 24 may also be used to communicate with IMD 16B. A user may use programmer 24 to retrieve information from IMD 16B regarding the performance of IMD 16B and to interact with programmer 24 to program, e.g., select parameters for, any additional therapies provided by IMD 16B. The programmer 24 also facilitates user interaction remotely via a networked computing device.

IMD 16A and 16B (collectively "IMD 16") may each include one or more local clocks (not shown in FIGS. 1 and 2). One such local clock is a system clock according to which the IMD 16 may perform sensing and therapy delivery. In order to reduce current drain by the clocking system within IMD 16, a low-power oscillator may be selected as the system clock. Low-power oscillators, however, suffer from inaccuracies due to poor long-term stability, temperature characteristics, and trim resolution. According to the techniques of this disclosure, IMD 16 includes calibration circuitry that periodically performs a calibration routine to calibrate the low-power local clock. The calibration of the local clock is performed with reference to a remote signal received from a high accuracy clock source. The low-power local clock may be powered continuously to control operation of IMD 16. By providing a low-power local clock that is periodically calibrated to maintain accuracy, the techniques of this disclosure may reduce total current drain associated with the clocking system in IMD 16 to less than 60 nA.

Figure 3:
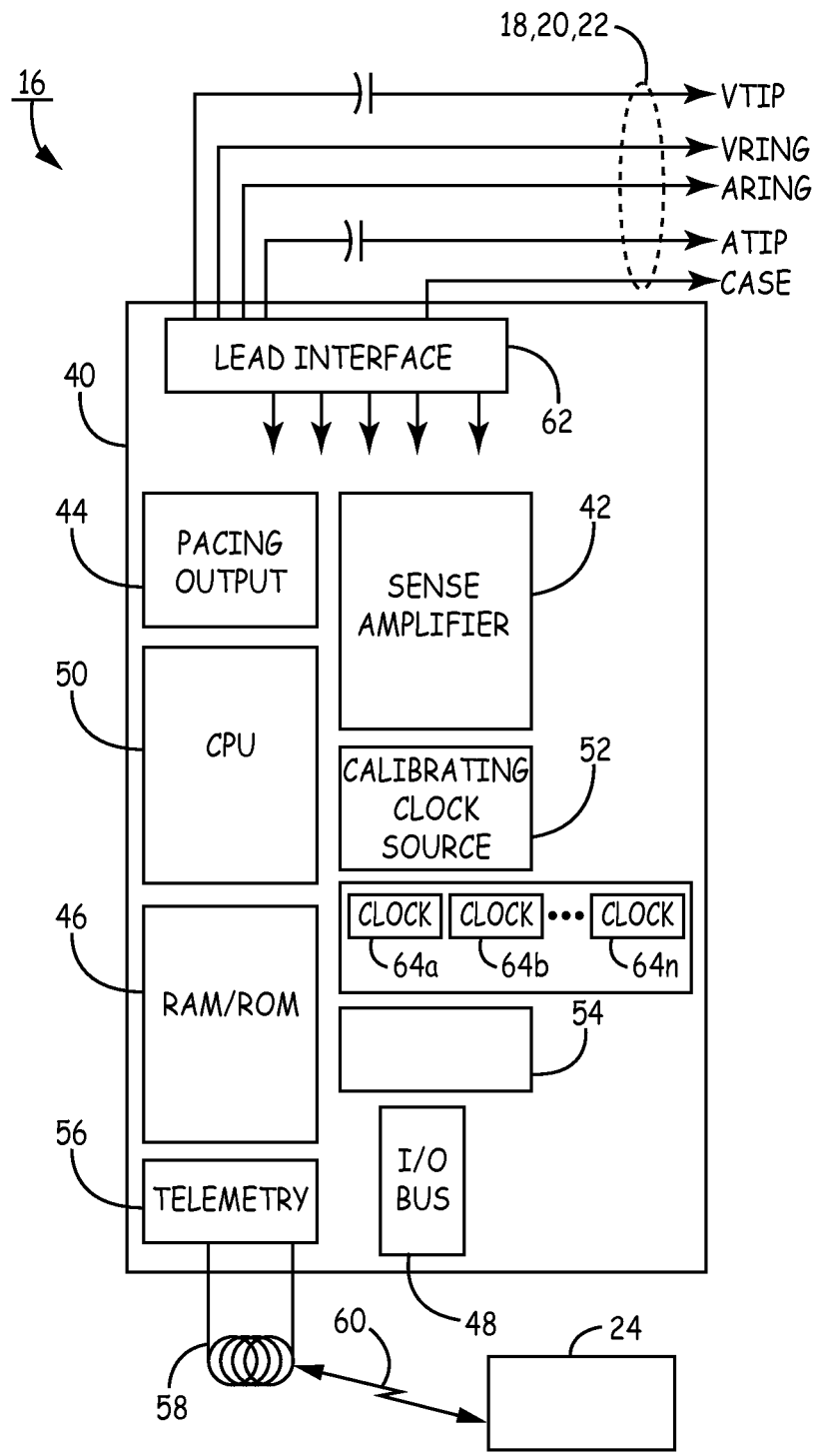
FIG. 3 is a block diagram of an embodiment of electronic circuitry that may be utilized within a device in accordance with the present disclosure.

FIG. 3 is a block diagram of an embodiment of electronic circuitry that may be utilized within a device such as IMD 16 in accordance with the present disclosure. It is common to provide circuitry in the IMD 16 that is clocked at multiple frequencies. For example, the IMD 16 is shown having circuitry 40 with different functionality to control therapy delivery and sensing functions. Portions of circuitry 40 may be of conventional design such as disclosed in U.S. Pat. No. 5,052,388 issued to Sivula et al. For example, circuitry 40 may include sense amplifier circuitry 42, stimulating pulse output circuitry 44, a random-access and/or read-only memory (RAM/ROM) unit 46, and an I/O Bus 48 all of which are well-known in the art.

Circuitry 40 includes one or more low-power clocks 64A-N (collectively, "low-power clock(s) 64"). The low power clocks 64 provide clock signals of differing frequencies as desired for operation of the various segments of circuitry 40. Circuitry 40 also includes a calibrating clock source 52 and a clocking circuit 54 for periodic calibration of the low-power clocks 64. In one example, the calibrating clock source 52 may be a high accuracy oscillator such as a crystal oscillator. In accordance with aspects of this disclosure, a single calibrating clock source 52 and the low-power clocks 64 are provided to reduce the current consumption of the circuitry 40. Therefore, rather than providing each of the low-power clocks 64 as a high accuracy clock for operation of each segment of the circuitry 40, the low-power clocks 64 are periodically tuned based on signals generated by the clock source 52. For example, the low-power clocks 64 may comprise extremely low power digitally trimmed oscillators, and may be built using adjustable current, voltage, resistor, capacitor, or number of stages to allow a delay time or clock period to be adjusted. As one example, one such low-power clock 64 may include a digital storage element that sets a value for a programmable value resistor used to generate a bias current. The bias current can be used to adjust delay time of two delay elements. The two delay elements may be configured such that one capacitor in one delay element is being charged up with current, while the other capacitor in the other delay element is being cleared. The two delay elements may create approximately equal delays that are used to define the low and high periods of the clock. In accordance with this example, such a low-power clock 64 may operate at 32 kHz with a current drain of about 50-100 nA.

Although the low-power clocks 64 are powered continuously to control operation of the various segments of circuitry 40, the current consumption of these low-power clocks 64 is considerably lower than that of the calibrating clock source 52. The calibrating clock source 52 and the clocking circuit 54 may be powered only during a calibration routine of the low-power clocks 64 to correct inaccuracies of the low-power clocks 64.

A central processing unit (CPU) 50 is also provided for executing instructions stored in memory, including memory unit 46, to cause IMD 16 and CPU 50 to perform various functions attributed to IMD 16 and CPU 50. Such functions include controlling sense amplifier circuitry 42 to monitor/sense signals associated with the electrical activity of the heart 12 and causing stimulating pulse output circuitry 44 to deliver stimulation therapy to heart 12 according to operational parameters or programs, which may also be stored in memory unit 46. Additionally, the CPU 50 controls a calibration routine for correcting inaccuracies of the low-power clocks 64. In one embodiment, the CPU 64 may issue instructions to clocking circuit 54 to initiate the calibration. The calibration routine may be performed for all clocks simultaneously, or in a serial order, or any other desired sequence. For example, one or more calibration intervals may be defined for each of the low-power clocks 64 based upon the sensitivity of each respective clock drift.

To operate IMD 16, a short term accuracy of approximately +/−1% may be sufficient to meet accuracy requirements of the multiple circuit segments of circuitry 40 over a heart rate pacing cycle or other short term timing requirements. Tighter accuracy of approximately +/−0.35% may be needed over the length of a day to enable or disable sensing and therapies at certain times of the day with an accuracy of approximately +/−5 minutes per day. Moreover, an accuracy equivalent to that of calibrating clock source 52 is required to achieve long term accuracy requirements of keeping track of time to within 5-10 minutes per year.

In accordance with the techniques described herein, the short term accuracy requirements may be achieved by periodically performing the calibration routine to calibrate each of the low-power clocks 64 based on calibrating clock source 52. The calibration determines a clock error of the low-power clocks 64. Operation of the low-power clocks 64 may be adjusted to compensate for the clock error.

The CPU 50 initiates the calibration routine by powering the clock source 52 and the clocking circuit 54. The calibration may be initiated in response to expiration of a predetermined time interval or at a pre-programmed or predefined time of day or in response to identification of an error in the clock signal of the low-power clocks 64. For example, the error may be detected following identification of misalignment between an active edge, e.g., falling clock edge or rising clock edge, of a local clock and an external device. In other examples, the CPU 50 may detect the error based on multiple failures in communication with an external device.

The clocking circuit 54 may be powered only periodically during the calibration routine to correct inaccuracies of the local clock. The clocking circuit 54 may perform the calibration routine according to a calibration period. For example, the clocking circuit 54 may be powered on for each calibration period of approximately 15 minutes to perform the calibration routine. In this way, the total clocking system current drain (including the low-power clocks 64 and the clocking circuit 54) in IMD 16 is minimized.

The clocking circuit 54 performs the calibration routine by powering on the calibrating clock source 52 and the one of the low-power clocks 64A-N that is selected for calibration at the start of the calibration routine, determining the frequencies of the calibrating clock source 52 and the low-power clock 64, deriving a calibration factor for calibrating the low-power clock 64 based on the accurate clock source 52, and disabling the calibrating clock source 52 at the end of the calibration routine. In response to a determination of an error in the clock signal generation of the low-power clock 64, the calibration factor is applied to adjust the operation of the low-power clock 64.

Figure 4:
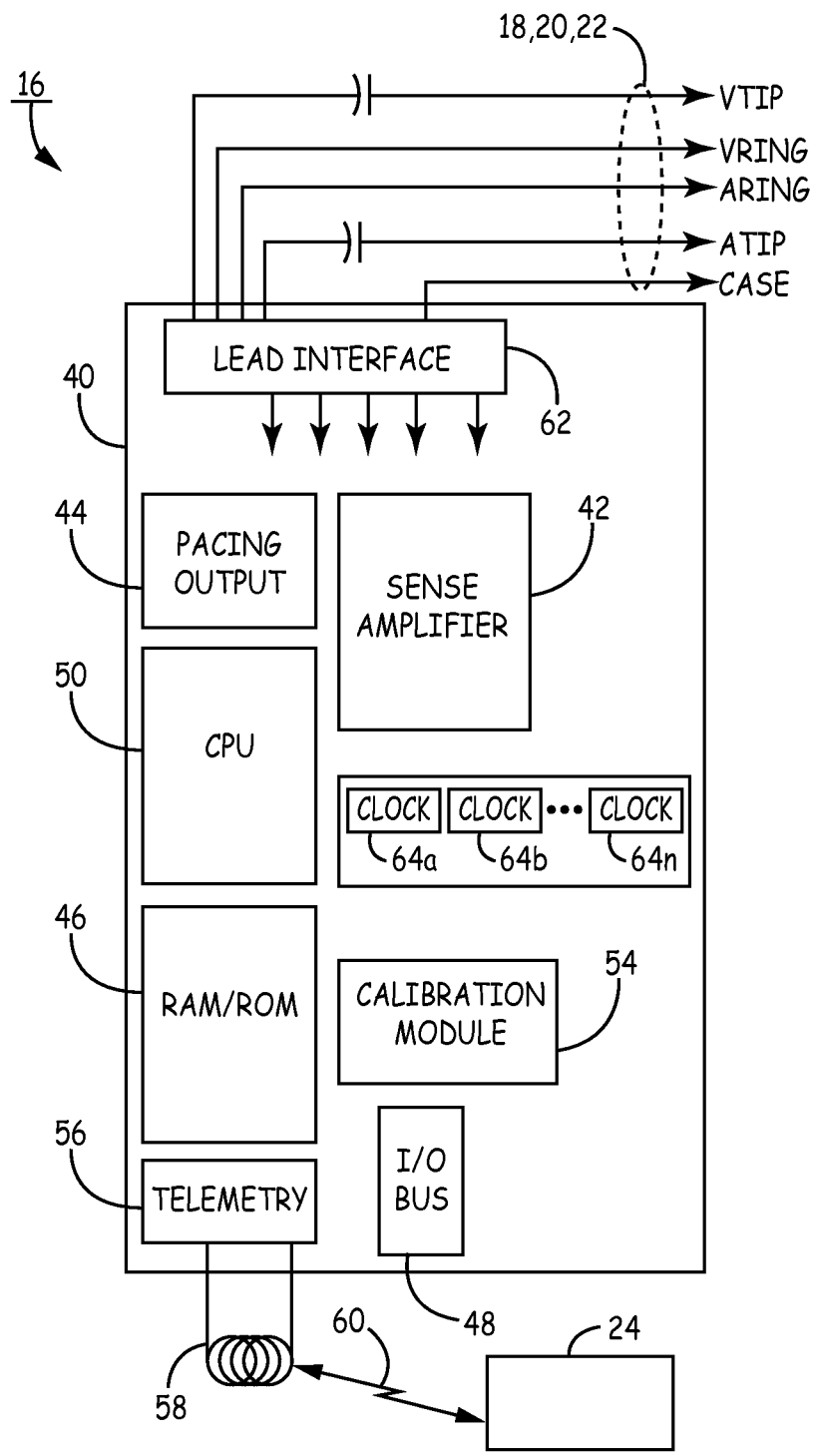
FIG. 4 is a block diagram of an alternative embodiment of electronic circuitry that may be utilized within a device in accordance with the present disclosure.

FIG. 4 is a block diagram of an alternative embodiment of electronic circuitry that may be utilized within a device such as IMD 16 in accordance with the present disclosure. The elements in the depicted circuitry 40b corresponding to those in FIG. 3 are numbered with identical reference designators. The reader is referred to the preceding description of FIG. 3 for a full discussion pertaining to those components.

In accordance with the embodiments of this disclosure, one or more low-power clocks 64A-N may be provided for controlling operation and functions of the circuitry components of IMD 16. The low-power clocks 64A-N may include one or more local clocks (not shown), e.g., system clock, for generating clock signals that control one or more circuits or functions of IMD 16.

A communication circuit such as telemetry system 56 may be provided to allow the device to communicate with external devices such as programmer 24 and other devices (FIG. 5) via antenna 58 and communication channel 60. In some embodiments, the IMD 16 receives signals for calibrating the low-power clocks 64A-N through the communication circuit.

As previously noted, circuitry 40 includes CPU 50 which may be an off-the-shelf programmable microprocessor, a micro-controller, or a custom integrated circuit. In accordance with embodiments of this disclosure, the CPU 50 issues instructions to the clocking circuit 54 to initiate a calibration routine. The instructions may be generated in response to receipt of a remote signal telemetered from an external device. Alternatively, the CPU 50 may coordinate the initiation of the calibration routine by the clocking circuit 54 in addition to communicating a request for the calibrating signal from an external device in response to expiration of a predetermined time interval or at a pre-programmed or predefined time of day or in response to identification of an error in the clock signal.

Sense amplifier circuit 42 receives electrical cardiac signals from leads 18, 20, 22. These signals are processed to detect the occurrence of specific cardiac electrical events, including atrial contractions (P-waves) and ventricular contractions (R-waves). Sense amplifier circuit 42 then provides event-indication signals to CPU 50 for use in controlling the synchronous stimulating operations of IMD 16 in accordance with common practice in the art. In addition, these event-indication signals may be stored as diagnostic data in RAM/ROM 46 and subsequently communicated via uplink transmission 60 to an external device such as programmer 24.

The low-power clocks 64A-N are powered continuously to provide clock signals for controlling the functions of the circuitry 40 such as sensing electrical activity and therapy delivery. In order to reduce current drain by the clocking system within IMD 16, the low-power clocks 64A-N utilize a low-power oscillator. Low-power oscillators, however, suffer from inaccuracies due to poor long-term stability, temperature characteristics, and trim resolution. According to the techniques of this disclosure, clocking circuit 54 periodically performs a calibration routine to calibrate the low-power system clock.

The clocking circuit 54 performs the calibration routine by determining a clock error of a given one or more local clocks of the low-power clocks 64A-N based on a difference between the given one or more of the local low-power clock(s) 64 A-N and the remote signal over a predetermined duration and adjusting operation of the local clock to compensate for the clock error. In some examples, the clocking circuit 54 may include a delta-sigma loop to perform the calibration routine by integrating the clock error over time to calculate a cumulative clock error of the local clock, and adjusting operation of the clock based on the magnitude and sign of the cumulative clock error. Calibrating the local clock with a delta-sigma loop reduces the clock error over time. This allows accurate adjustment of the system clock to compensate for errors due to trim resolution, circuit noise and temperature. As such, the techniques may reduce total clocking system current drain in IMD 16 to less than 60 nA. IMD 16 may include multiple clocking circuits to calibrate other clocks that may be included in IMD 16, such as a telemetry polling clock and a telemetry linking clock used to operate telemetry between IMD 16 and, e.g., programmer 24.

Other components and subsystems may be provided within the scope of the current invention, including activity sensors and/or any other type of subsystem known for use within an IMD. The various components are powered by a power source such as a battery (not shown) that is contained within the hermetic enclosure of IMD 16 in accordance with common practice in the art.

Figure 5:
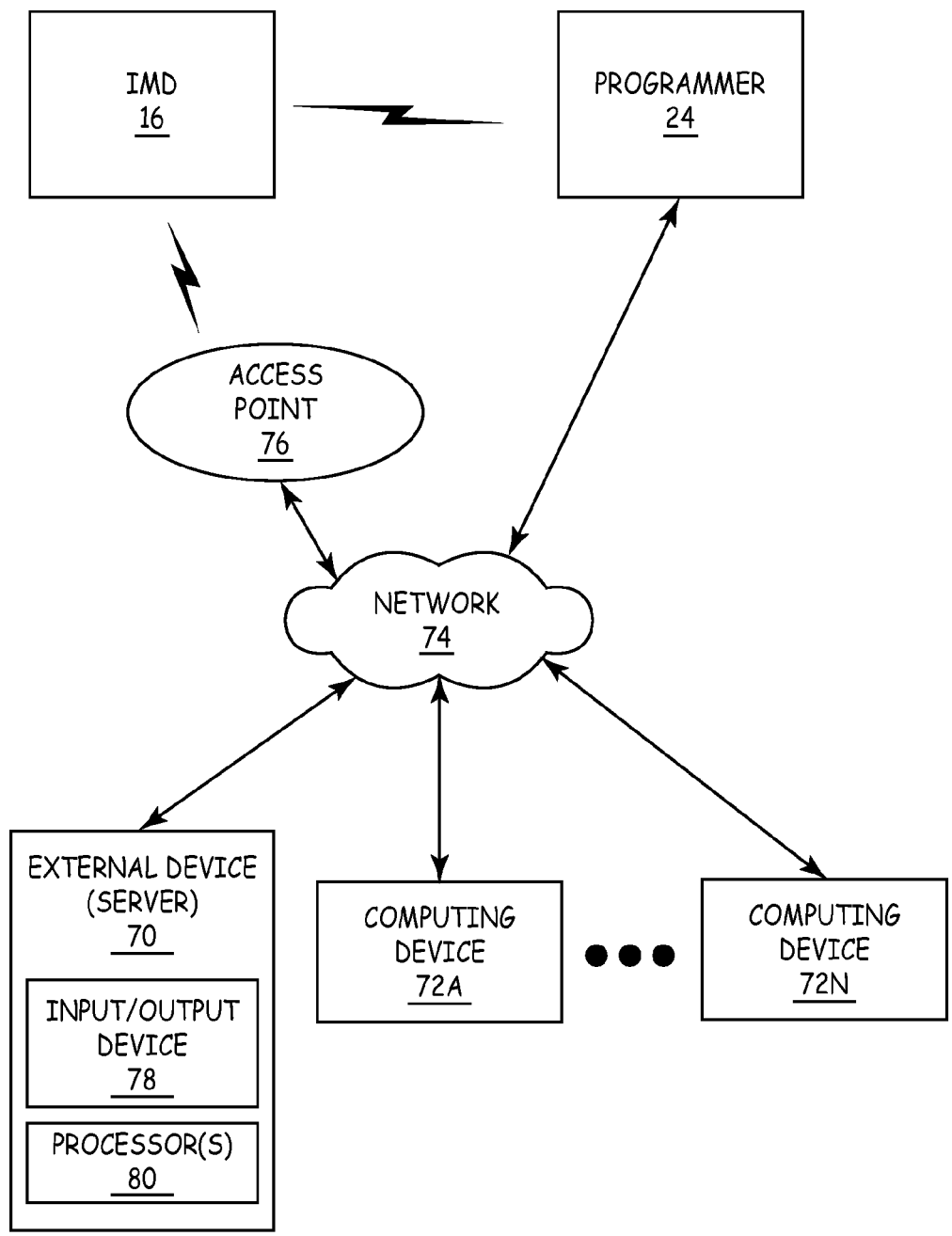
FIG. 5 is a block diagram illustrating an embodiment of a network system that includes an implantable medical device coupled to a plurality of external devices.

FIG. 5 is a block diagram illustrating an embodiment of a network system that includes IMD 16 coupled to a plurality of external devices including programmer 24, server 70, and one or more computing devices 72A-72N. The server 70 and computing devices 72A-72N may be coupled to the IMD 16 and programmer 24 via a network 74. In this example, IMD 16 may use its telemetry module 56 to communicate with programmer 24 via a first wireless connection, and to communicate with an access point 76 via a second wireless connection. In the example of FIG. 5, access point 76, programmer 24, server 70, and computing devices 72A-72N are interconnected, and able to communicate with each other, through network 74. In some cases, one or more of access point 76, programmer 24, server 70, and computing devices 72A-72N may be coupled to network 74 through one or more wireless connections. IMD 16, programmer 24, server 70, and computing devices 72A-72N may each comprise one or more processors, such as one or more microprocessors, DSPs, ASICs, FPGAs, programmable logic circuitry, or the like, that may perform various functions and operations, such as those described herein.

Access point 76 may comprise a device that connects to network 74 via any of a variety of connections, such as telephone dial-up, digital subscriber line (DSL), or cable modem connections. In other examples, access point 76 may be coupled to network 74 through different forms of connections, including wired or wireless connections. In some examples, access point 76 may be co-located with patient 14 and may comprise one or more programming units and/or computing devices (e.g., one or more monitoring units) that may perform various functions and operations described herein. For example, access point 76 may include a home-monitoring unit that is co-located with patient 14 and that may monitor the activity of IMD 16. In some examples, server 70 or computing devices 72 may control or perform any of the various functions or operations described herein.

In some cases, server 70 may be configured to provide a secure storage site for data that has been collected from IMD 16 and/or programmer 24. Network 74 may comprise a local area network, wide area network, or global network, such as the Internet. In some cases, programmer 24 or input/output device 78 may assemble data in web pages or other documents for viewing by trained professionals, such as clinicians, via viewing terminals associated with computing devices 72A-72N. The illustrated system of FIG. 5 may be implemented, in some aspects, with general network technology and functionality similar to that provided by the Medtronic CareLink® Network developed by Medtronic, Inc., of Minneapolis, Minn.

In some examples, processor(s) 80 of server 204 may be configured to provide some or all of the functionality ascribed to IMD 16 and CPU 50 herein. For example, processor 80 may receive one or more signals from sensing amplifier 42 or other information regarding sensed parameters from IMD 16 via access point 76 or programmer 24 and network 74. In some examples, server 70 relays received signals provided by one or more of IMD 16 or programmer 24 to one or more of computing devices 72 via network 74. In other examples, a processor of a computing device 72 may provide some or all of the functionality ascribed to IMD 16 and CPU 50 in this disclosure.

In accordance with embodiments of this disclosure, a remote signal may be provided to the IMD 16, via wireless connection, by one of the external devices associated with the system of FIG. 5. The remote signal may include a clock signal, or a signal such as a data signal, or a control/command signal. Such remote signal may include the radio frequency (RF) synchronization data stream that may be included in the header of a telemetry communication message. In accordance with embodiments of this disclosure, the remote signal may be utilized by the IMD circuitry for calibration of the local clock of the IMD 16. Such a remote signal may be generated by the external device as a function of a high accuracy oscillator, such as a crystal oscillator, that runs on a substantial amount of current, e.g., between 0.5 and 1 microampere ($\mu$A). Unlike conventional IMDs that include the high accuracy oscillators in the IMD circuitry, techniques in accordance with the present disclosure reduce the number of high accuracy oscillators (or eliminate them entirely) from the IMD circuitry. Reducing or eliminating the high accuracy oscillators facilitates a reduction in IMD circuitry cost and size because the high accuracy oscillators are large (consuming about 10% of module area) and expensive (approximately 4%-10% device cost) in comparison to the low accuracy oscillators.

As discussed above, the clocking system of IMD 16 includes low-power clocks 64A-N and clocking circuit 54. In some examples, the low-power clocks 64A-N that compose the clocking system of IMD 16 include, for example, a telemetry polling clock, a telemetry linking clock, a CPU clock, and a rate limit clock. Each of the local clocks may be associated with a separate oscillator, each operating at different frequencies with different accuracies and different power requirements. A majority of the clocks within the clocking system may be able to operate at a very low duty cycle to minimize power. For example, these clocks may be turned on only when needed and shut down with as close to zero current as possible for the remainder of the time.

A minimum of one local clock, however, must remain continuously enabled to facilitate sensing and therapy delivery, and to enable other features at certain times. This local clock serves as a system clock. Historically, a high accuracy oscillator, such as a crystal oscillator, has been used as the system clock as it provides a high degree of accuracy (+/−0.01%) at a moderate current drain. In order to further reduce current drain of the clocking system, a low-power oscillator may be selected as the system clock—the current drain of the low-power oscillator is magnitudes (e.g., 5 times) lower compared to the current drain of the crystal oscillator. Low-power oscillators, however, suffer from inaccuracies due to poor long-term stability, temperature characteristics, and trim resolution.

Figure 6:
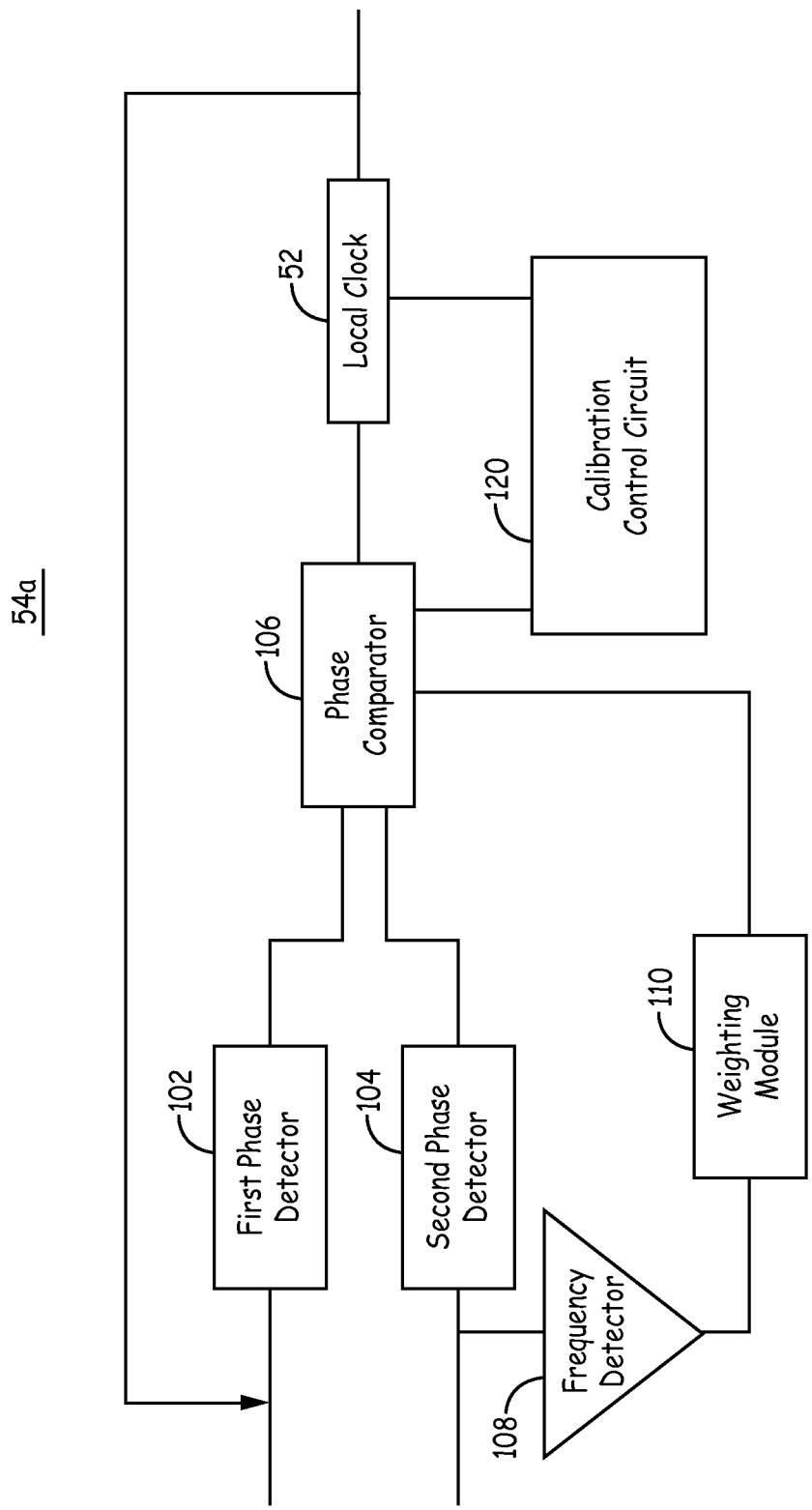
FIG. 6 depicts an exemplary embodiment of a clocking circuit is depicted.

Turning now to FIG. 6, an exemplary embodiment of a clocking circuit is depicted. Clocking circuit 54a is coupled to low-power clocks 64A-N that generate clock signals utilized for controlling functions of IMD 16. Although not intended to be limiting, the description of the calibration of the low-power clocks 64A-N is discussed with relation to calibration of a single one of the low-power clocks 64A-N. However, it should be noted that the clocking circuit 54a may function to simultaneously calibrate all the low-power clocks 64A-N in one implementation. Moreover, providing multiple clocking circuits 54a associated with individual or groups of low-power clocks 64A-N is also within the scope of this disclosure.

The clocking circuit 54a includes a first signal counter 102, a second signal counter 104, a comparator 106, and calibration control circuit 120. The calibration control circuit initializes the calibration routine and makes appropriate adjustments to low-power clocks 64 based on results of the calibration routine. In essence, the clocking circuit 54a periodically performs a calibration routine to detect a clock error of low-power clock 64.

Clocking circuit 54a performs the calibration routine by comparing a clock signal generated by local low-power clock 64 to a remote clock signal generated by an external signal generator that is located remote to the IMD 16 to identify whether a clock error in local low-power clock 64 is present. The initiation of the calibration routine is also coordinated with the external device such as programmer 24. Prior to initiating the calibration routine, either the IMD 16 or the external device communicates to the other that criteria for initiating the calibration routine is met and in response to an acknowledgment that the calibration routine is about to begin, the external device transmits a remote clock signal to the IMD 16. As discussed in various embodiments, the external signal generator may reside within the IMD 16. The remote clock signal is received by the second signal counter 104.

The first signal counter 102 is connected to the local low-power clock 64. A clock signal generated by low-power clock 64 is provided to the first signal counter 102 triggered by activation of the calibration routine. Control of the calibration routine including aspects such as when to initiate the routine, when to terminate the routine, processing of the results of the calibration routine and any other matters associated with the calibration of low-power clock 64 may be handled by the CPU 50 or a dedicated processor (not shown) that is programmed to control the calibration. For ease of discussion, this disclosure contemplates that the instructions to control and handle the calibration are handled by the CPU 50. As such, the CPU 50 issues an instruction to initiate the calibration routine which causes the low-power clock 64 to generate and provide clock signals to the first signal counter 102.

In response to receipt of the clock signals from the local low-power clock 64, the first signal counter 102 counts the clock cycles of the clock signal. The counting of the number of clock cycles of the remote clock signal by the second signal counter 104 is initiated simultaneously with the counting of the number of clock cycles of the low-power clock 64 signal.

In one embodiment of the calibration routine, the clock signals of the local low-power clock 64 are provided for a fixed number of clock cycles of the signals generated by low-power clock 64. In other words, the CPU 50 is programmed with a target number of clock cycles and upon the first signal counter 102 reaching that number, an instruction is issued to second signal counter 104 to provide the number of clock cycles measured over the duration corresponding to a predetermined number of clock cycles measured by the first signal counter 102.

Counting by the second signal counter 104 is therefore halted upon reaching the predetermined number of clock cycles by the first signal counter 102. In an alternate embodiment, the converse relationship may be utilized. That is, the CPU 50 may be programmed with a target number of clock cycles and upon the second signal counter 104 reaching that number, an instruction is issued to first signal counter 102 to provide the number of clock cycles measured over the duration corresponding to the predetermined number of clock cycles measured by the second signal counter 104.

Both the first signal counter 102 and the second signal counter 104 are connected to comparator 106. In response to the first signal counter 102 (or second signal counter 104) counting up or down to the predetermined number of clock cycles, the other of the second signal counter 104 (or first signal counter 104) also stops counting and both count numbers are provided to the comparator 106. A calibration factor is computed by the comparator 106. The calibration factor is computed by comparing the number of clock cycles counted by the first signal counter 102 against the number of clock cycles counted by the second signal counter 104. The calibration factor may be computed as follows:

$$\text{Calibration Factor(CF)} = \text{Remote Clock Cycles(RCC)} / \text{Local Clock Cycles(LCC)}.$$

In the equation: RCC is the count of the number of cycles from the remote clock over a give duration and LCC is the number of clock cycles of the local low-power clock over the given duration.

In some embodiments, the clocking circuit 54a may also include a frequency detector 108, and a weighting module 110. The frequency detector 108 evaluates the frequency component of a received remote signal to derive a comparative difference between the frequency of the received signal and a predetermined frequency (or frequency range) of the clock signal of the local low-power clock 64. For example, the local clock signal may have a frequency range within +/−2% of 32 KHz whereas the remote signal may have a 64 KHz frequency, for example. The Frequency detector 108 provides an indication of the magnitude of the received signal frequency to the weighting module 110. The weighting module 110 compares the frequency of the received signal to the desired frequency of the signal generated by the low-power clock 64. In response to the frequency of the received signal being equal to the desired frequency of the signal generated by low-power clock 64, a weighting value of 1 is assigned to the received signal and this value is issued to the comparator. In response to the frequency of the received signal being less than or equal to the desired frequency of the signal generated by low-power clock 64, a weighting value other than 1 is calculated by the weighting module 110. Stated simply, the weighting value is a number that is a factor of the frequency of the received signal such that the product of the weighting value and the desired frequency of the signal generated by the low-power clock 64 is equal to the frequency of the received signal. The computed weighting value is provided to the comparator 106.

Embodiments that include computation of a weighting value are useful in implementations where the frequency of the remote signal is unknown or not equal to the frequency of the target signal generated by the local low-power clock 64. In such embodiments, the calibration factor may be calculated in accordance with the following equation:

Calibration Factor(CF)=[Remote Clock Cycles(RCC)/Local Clock Cycles(LCC)]/WF.

In the equation: WF is the Weighting Factor and (WF)=(Frequency of Remote Clock (FRC)/Frequency of Local Clock (FLC).

The inventor of the present disclosure has also observed that the accuracy of the calibration results may also be dependent on the duration of the calibration cycle. For instance, calculating the calibration factor based on clock cycle counts for the local clock and the remote clock over a first duration will yield a better result that a calculation of the calibration factor over a second duration that is shorter than the first duration. As such, the predetermined number of clock cycles counted by the second signal counter 104 and corresponding to the predetermined duration over which the first signal counter 102 counts the cycles of the local clock cycles may be determined by the equation:

Target Accuracy(ppm)=[2/(WFI*Calcount)]*1e6.

In the equation, ppm is parts per million, and Calcount is the number of clock cycles counted by the second signal counter 104. The Target Accuracy is expressed as parts per million (ppm). For example, if the target accuracy is 0.1%, the clock is 1000 ppm or if the target accuracy is 1%, then the accuracy is 1%.

A weighting value of 1 denotes that the frequencies of the local clock signal and the remote signal are identical. As such, a 1:1 correspondence between the count of clock cycles is expected if the local clock is functioning accurately. The correspondence between the count of clock cycles of the local clock signal to the count of clock cycles of the remote signal is modified in the event that the weighting value is greater than or less than 1. For example, a weighting value of 2 indicates that the frequency of the remote signal is double that of the local clock. Therefore, the comparison will factor in this difference so as not to erroneously double the speed of the local clock.

While the exemplary clocking circuit of FIG. 6 is illustrated in the context of single local low-power clock 64, it should be noted that the circuit may be implemented with other local clocks of the IMD 16. Moreover, rather than a single local clock, multiple local clocks (not shown) of the IMD 16 may be substituted for the low-power clock 64 by implementing a switching mechanism that connects each individual one of such plurality of local clocks for calibration sequentially.

Figure 7:
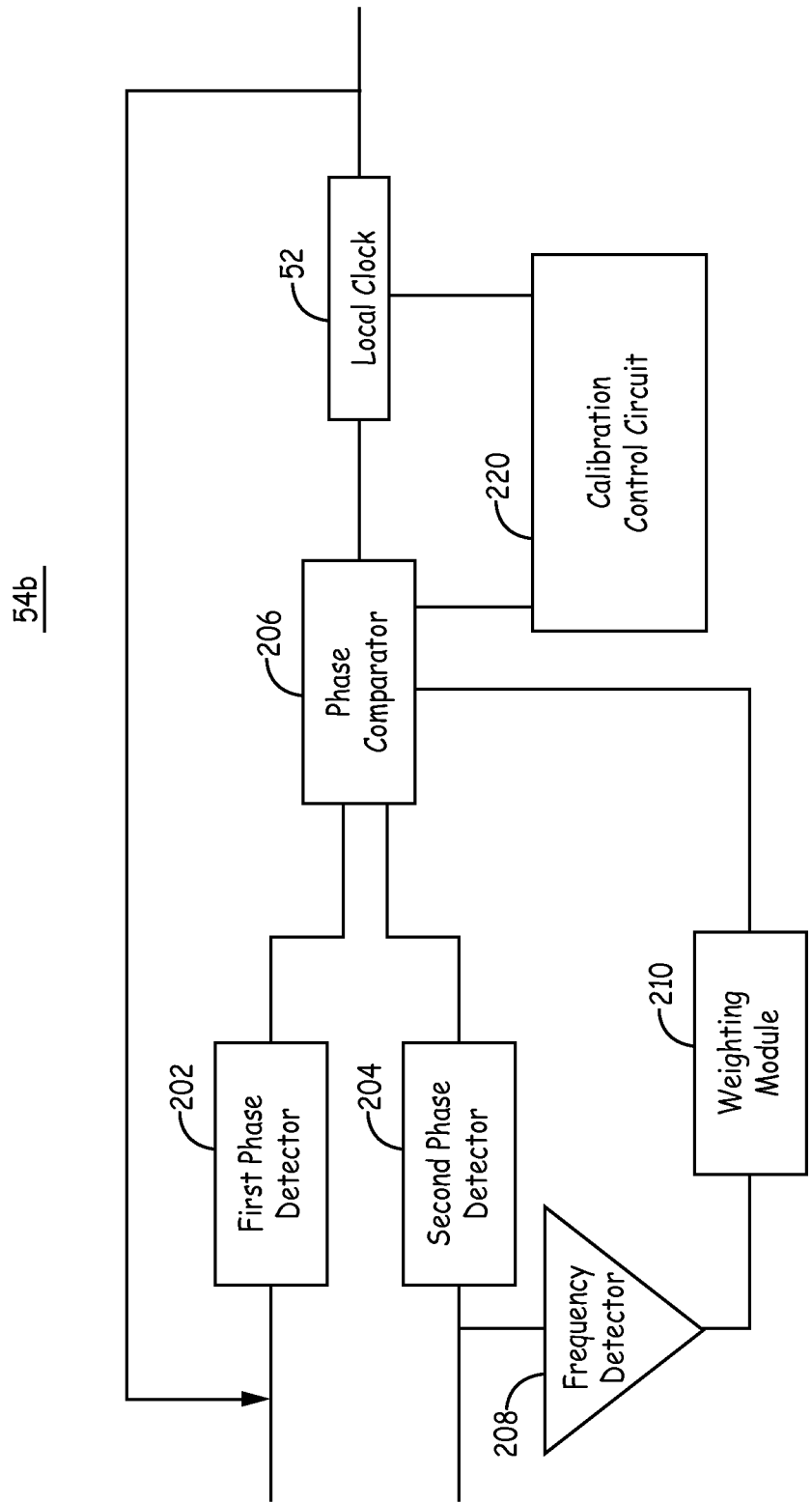
FIG. 7 illustrates an alternative clocking circuit in accordance with embodiments of this disclosure.

FIG. 7 illustrates an alternative clocking circuit in accordance with embodiments of this disclosure. This embodiment may suitably be utilized in embodiments where the calibrating signal is a signal other than a clock signal. A clocking circuit 54b is provided having a calibration control circuit 220 that initializes the calibration routine and makes appropriate adjustments to low-power clock 64 based on results of the calibration routine. The clocking circuit 54b further includes a first phase detector 202 and a second phase detector 204. The first phase detector 202 and the second phase detector 204 are coupled to a phase comparator 206. First phase detector 202 receives a clock signal from the local low-power clock 64 while second phase detector 204 receives a remote signal from an external device. The remote signal may be a clock signal, a data signal, an instruction signal, a power signal or any other wireless signal telemetered from the external device to the IMD 16.

In response to initiation of a calibration routine, the first phase detector 202 is programmed to detect a phase of the clock signal generated by low-power clock 64. Second phase detector 204 is programmed to detect a phase of the remote signal received from the external device. A signal phase of a clock signal or a remote signal may be detected by identifying either a rising edge of the signal or a falling edge of the signal. Both the first phase detector 202 and the second phase detector 204 output to the phase comparator 206 the respective identified phases of the low-power clock 64 signal and the remote signal. In addition, a relative delay between the determination of the phase of the local clock signal and the remote signal is identified by the phase comparator 206. In other words, in response to the receipt of each of the detected rising (or falling) edges, the phase comparator 206 also evaluates the delay between the edges of the low-power clock 64 signal and the remote signal.

The clock signal of low-power clock 64 is deemed to be out of phase when the phase of the clock signal is misaligned in comparison with the phase of the remote signal. The clock signal may be deemed to be out of phase when the delay indicates that the edge (rising or falling) of a clock signal is leading or lagging as compared to a corresponding edge (rising or falling) of a remote signal.

In response to detecting a phase discrepancy between the clock signal and the remote signal, the phase comparator 206 generates a calibration factor that is applied to the low-power clock 64 to compensate for the phase discrepancy. The calibration factor may be stored in a memory of IMD 16 and is applied to delay the pulses of low-power clock 64 in response to the clock signal leading the remote signal or to speed up the pulses of low-power clock 64 in response to the clock signal lagging the remote signal. The determination of the calibration factor may be performed in an iterative manner, i.e., a first calibration factor is calculated following a first iteration and utilized in a second iteration to determine whether a modification should be made to the first calibration factor and if so, the modified calibration factor is utilized in a third iteration and so on and so forth. The premise for determining the calibration factor is that a calibration factor is calculated such that when applied to the local clock generator, it causes the clock signal of low-power clock 64 to be in phase, or substantially in phase (e.g., within a range of about 1%-5%) with the remote signal.

The signal generated by low-power clock 64 may be delayed or sped up by coupling the signal path to one or more delay elements or decoupling the signal path from one or more delay elements. Delay elements are known in the art and it is not believed necessary to detail the operation of such elements. For example, the output of low-power clock 64 may be coupled to delay elements such as circuits including transistors and/or a set of dynamic latches.

In alternative embodiments, a frequency detector 208 and a weighting module 210 may be included in the clocking circuit 54*b*. The frequency detector 208 functions similarly to the frequency detector 108 of FIG. 6 in evaluating the frequency component of a received remote signal to determine whether the frequency of the received signal is the same as a predefined signal of the local low-power clock 64. Frequency detector 208 provides an indication of the magnitude of the received signal frequency to the weighting module 210. In response to the frequency of the received remote signal being equal to the desired frequency of the signal generated by low-power clock 64, a weighting value of 1 is assigned to the received remote signal and this value is issued to the phase comparator 206. In response to the frequency of the received signal being less than or equal to the desired frequency of the signal generated by low-power clock 64, a weighting value other than 1 is calculated by the weighting module 210 and provided to the comparator 206.

In response to the weighting value being 1, the phase comparator performs a 1:1 comparison between the clock signal and the remote signal. In other words, the weighting value of 1 indicates that each clock cycle should correspond to each cycle of the remote signal. Conversely, a weighting value greater than or less than one (1) indicates that there is no one-to-one correspondence between the frequency of the clock signal and the remote signal and therefore all the edges are not expected to line up. Therefore, the comparator utilizes the weighting value to determine which cycle of the remote signal will align with a cycle of the clock signal and evaluates the relative position of the edge of that cycle to the edge of the clock signal. A calibration factor may then be computed in response to the edge of the clock signal leading or lagging the edge of the remote signal.

Figure 8:
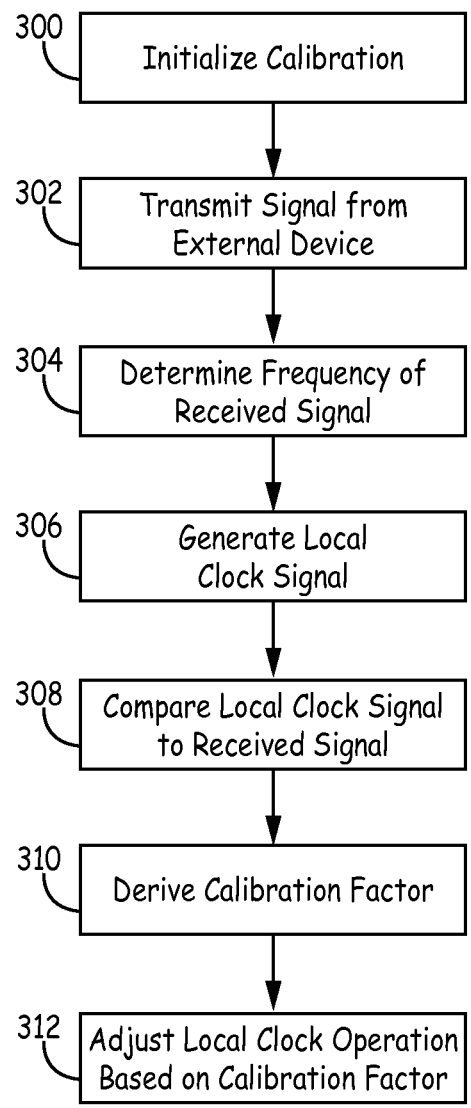
FIG. 8 depicts a flow chart including the tasks of a calibration routine that may be performed by a system that includes an external device and an implantable medical device in accordance with embodiments of the present disclosure.

FIG. 8 depicts a flow chart including the tasks of a calibration routine that may be performed by a system that includes an external device and IMD 16 in accordance with embodiments of the present disclosure.

The calibration routine may be initialized (task 300) in one of many ways, with the instructions to initialize being provided by the IMD 16 or by the external device such as the programmer 24. For example, the calibration routine may be initialized at a predetermined time of day. In another example, the calibration routine may be performed periodically following the lapse of a predetermined time interval, such as every five minutes or five hours or five days or five weeks. In another example, the IMD may initialize the calibration routine in response to a communication error. In yet another example, the phase detection may be performed periodically in response to receipt of a remote signal and the calibration routine initiated upon detection of the clock signal of low-power clock 64 being out of phase with the remote signal.

Upon initialization of the calibration routine, a calibrating signal is obtained (302). The calibrating signal may be received from an external device, such as programmer 24, in response to a coordinated request from IMD 16. In other embodiments, the calibrating signal may be provided by an accurate clock source residing in IMD 16. The calibrating signal may be a clock signal while, in other embodiments, the calibrating signal may be a remote signal such as a power signal, or a control/command signal, or a data signal.

The calibrating signal may be provided having an identical target frequency of the local clock signal or it may have a differing frequency. Accordingly, an alternate embodiment of the method may include a task to determine the frequency of the received signal (304).

Simultaneous with the receipt of the calibrating signal, a clock signal (first clock signal) may also be generated by the local clock of the IMD 16 (306). The generation of the first clock signal by the IMD 16 may also be performed in response to initialization of the calibration routine.

The clock signal generated by the local clock and the signal received from the external device are compared to determine the accuracy of the local low-power clock (308). The comparison may be based on the relative positions of the clock cycles such as whether the cycles overlap one another. In another embodiment, the comparison may be based on a count of the clock cycles. The comparison of the clock cycles may be adjusted based on a difference between frequencies as discussed in this disclosure.

A calibration factor is generated in response to the comparison of the clock signal and the received signal (310). The calibration factor may be implemented to adjust the generation of the clock signal by the local clock (312). For example, the calibration factor may cause an adjustment of the frequency of the clock signal or the calibration factor may cause the coupling of one or more delay elements to adjust the timing of the clock signals.

The flow charts, techniques and technologies presented herein are intended to illustrate the functional operation of an exemplary device, and should not be construed as reflective of a specific form of software, firmware or hardware necessary to practice the invention. It is believed that the particular form of software, firmware, and hardware will be determined by the particular system architecture employed in the external or implantable medical device. For example, an embodiment of a system or a component may employ various integrated circuit components, e.g., memory elements, digital signal processing elements, logic elements, look-up tables, or the like, which may carry out a variety of functions under the control of one or more microprocessors or other control devices. To the extent that there is any ambiguity or inconsistency between the text and the circuit symbols depicted in the figures, the figures will be deemed to control.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The methods described in conjunction with flow charts may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The connecting lines shown in the various figures contained herein are intended to represent example functional relationships and/or physical couplings between the various elements. It should be noted that many alternative or additional functional relationships or physical connections may be present in an embodiment of the subject matter. Furthermore, it should be appreciated that the processes may include any number of additional or alternative tasks, the tasks shown in the flowchart need not be performed in the illustrated order, and the process may be incorporated into a more comprehensive procedure or process having additional functionality not described herein.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

The invention claimed is:

1. An implantable medical device, comprising:
   a first clock source configured to generate a first clock signal;
   a second clock source configured to generate a second clock signal; and
   a clocking circuit coupled to the first clock source and the second clock source, wherein the clocking circuit is configured to perform a calibration routine including comparing the first clock signal to the second clock signal, derive a weighing factor based on the relative magnitude of the first clock signal and the second clock signal, and generate a calibration factor based on the comparison and the weighting factor for calibrating the first clock source relative to the second clock source during a calibration routine.

2. The implantable medical device of claim 1, wherein the clocking circuit is configured to simultaneously compute a number of clock cycles of each of the first clock signal and the second clock signal during a first time interval and to generate the calibration factor based on the relative difference in the computed count of the clock cycles of the first clock signal and the second clock signal.

3. The implantable medical device of claim 2, wherein the clocking circuit is configured to determine a frequency of the second clock signal to determine whether the frequency is within a predetermined frequency range with respect to a frequency of the first clock signal.

4. The implantable medical device of claim 3, wherein the clocking circuit compares the computed number of clock cycles of the first clock signal to the second clock signal in response to the frequency being within the predetermined frequency range.

5. The implantable medical device of claim 3, wherein the clocking circuit compares the computed number of clock cycles of the first clock signal to a weighted count of the computed number of second clock signal cycles in response to the frequency falling outside of the predetermined frequency range.

6. The implantable medical device of claim 5, wherein the weighted count of the computed number of second clock signal cycles is computed based on the relative difference between the frequency of the second clock signal and the first clock signal.

7. The implantable medical device of claim 3, wherein the predetermined frequency has an upper limit and a lower limit based on a frequency of the local clock signal.

8. The implantable medical device of claim 3, wherein the upper limit and the lower limit are based on a target frequency range of the local clock signal.

9. The implantable medical device of claim 1, further comprising a calibration control circuit for generating a command signal to initiate the calibration routine.

10. The implantable medical device of claim 9, wherein the command signal is generated in response to expiration of a predetermined time interval.

11. The implantable medical device of claim 9, wherein the command signal is generated at a predefined time of day.

12. The implantable medical device of claim 1, wherein the clocking circuit is configured to compute a number of active edges of the first clock signal and the second clock signal during a fixed time interval and to generate the calibration factor based on the computed number of active edges.

13. The implantable medical device of claim 1, wherein the local clock generator is adjusted based on the calibration factor to generate an updated first clock signal.

14. The implantable medical device of claim 1, wherein the clocking circuit includes:
   a first signal counter for receiving the first clock signal and counting the number of cycles of the first clock signal in a first duration;
   a second phase detector for receiving the second clock signal and simultaneously counting the number of cycles of the second clock signal in a second duration; and
   a phase comparator to generate the calibration factor based on a comparison of the number of cycles counted by the first signal counter during the given duration and the number of cycles counted by the second signal counter.

15. The implantable medical device of claim 14, wherein the first duration and the second duration are identical.

16. The implantable medical device of claim 14, wherein the first duration and the second duration are measured concurrently.

* * * * *